United States Patent [19]
Cragg et al.

[11] Patent Number: 6,146,373
[45] Date of Patent: *Nov. 14, 2000

[54] CATHETER SYSTEM AND METHOD FOR INJECTION OF A LIQUID EMBOLIC COMPOSITION AND A SOLIDIFICATION AGENT

[75] Inventors: Andrew H. Cragg, Edina, Minn.; Richard J. Greff, St. Pete Beach, Fla.; Robert Pecor, Aliso Viejo, Calif.; John Perl, Cleveland Heights, Ohio; Blair Walker, Lake Forest; George Wallace, Coto De Caza, both of Calif.

[73] Assignee: Micro Therapeutics, Inc., San Clemente, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/953,149

[22] Filed: Oct. 17, 1997

[51] Int. Cl.⁷ .................................................. A61M 25/00
[52] U.S. Cl. ................................ 604/523; 604/48; 604/19
[58] Field of Search ................................ 604/264, 48, 49, 604/52, 53, 56, 265, 280, 283, 19, 507, 508, 518, 93, 523, 533, 500, 93.01; 600/433, 435, 139; 606/1, 194, 191, 192, 198, 200

[56] References Cited

U.S. PATENT DOCUMENTS

| | | | |
|---|---|---|---|
| 4,631,188 | 12/1986 | Stoy et al. . | |
| 4,819,637 | 4/1989 | Dormandy, Jr. et al. | 128/325 |
| 5,041,090 | 8/1991 | Scheglov et al. . | |
| 5,156,596 | 10/1992 | Balbierz et al. | 604/164 |
| 5,207,648 | 5/1993 | Gross | 604/164 |
| 5,395,353 | 3/1995 | Scribner | 604/264 |
| 5,443,454 | 8/1995 | Tanabe et al. . | |
| 5,580,568 | 12/1996 | Greff et al. | 424/423 |
| 5,667,767 | 9/1997 | Greff et al. | 424/9.411 |
| 5,695,480 | 12/1997 | Evans et al. | 604/264 |
| 5,702,361 | 12/1997 | Evans et al. | 604/53 |
| 5,733,267 | 3/1998 | Del Toro | 604/280 |
| 5,776,097 | 7/1998 | Massoud | 604/49 |
| 5,795,331 | 8/1998 | Cragg et al. | 604/96 |
| 5,830,178 | 11/1998 | Jones et al. | 604/49 |
| 5,921,954 | 7/1999 | Mohr, Jr. et al. | 604/53 |
| 6,015,424 | 4/2000 | Rosenbluth et al. | 606/200 |
| 6,051,607 | 4/2000 | Greff | 514/546 |

FOREIGN PATENT DOCUMENTS

| | | |
|---|---|---|
| 0747014 | 11/1996 | European Pat. Off. . |
| 95/25480 | 3/1995 | WIPO . |
| 96/18343 | 12/1995 | WIPO . |

OTHER PUBLICATIONS

Marks, Michael P., et al., *A Mechanically Detachable Coil for the Treatment of Aneurysms and Occlusion of Blood Vessels*, AJNR Am J Neuroradiol 15:821–827, May 1994.

Sadato, Akiyo, et al., *Immediately Detachable coil for Aneurysm Treatment*, AJNR 16:1459–1462, Aug. 1995.

Reidy, John F., et al., *Interlocking Detachable Platinum Coils A Controlled Embolization Device: Early Clinical Experience*, 19:85–90, 1996.

Primary Examiner—Corrine McDermott
Assistant Examiner—Cris L. Rodriguez
Attorney, Agent, or Firm—Burns, Doane, Swecker & Mathis, L.L.P.

[57] ABSTRACT

A catheter according to the present invention includes a multiple lumen catheter for delivery of a liquid embolic composition through a first lumen and delivery of a solidification agent through a second lumen. The catheter allows adjustment of the relative longitudinal position of the two lumens to control the solidification of the embolic composition within a blood vessel. The multiple lumen catheter system is used by inserting the catheter endovascularly into an aneurysm site and injecting a liquid embolic composition through the first lumen while injecting a solidification agent through the second lumen to wash the area of the aneurysm of blood which has become saturated with solvent, while replacing it with a fresh solidification agent. The controlled solidification of the liquid embolic composition by use of the solidification agent allows the aneurysm to be filled precisely and rapidly even when the aneurysm is located such that gravity does not cause the liquid embolic composition to flow into the aneurysm.

11 Claims, 3 Drawing Sheets

CATHETER SYSTEM AND METHOD FOR INJECTION OF A LIQUID EMBOLIC COMPOSITION AND A SOLIDIFICATION AGENT

BACKGROUND OF THE INVENTION

1. Field Of The Invention

The invention relates to a catheter system and method for combined injection of a liquid embolic composition and an embolic solidification agent, and more particularly, to a catheter system including a multiple lumen catheter for injection of a liquid embolic composition through a first lumen and an embolic solidification agent through a second lumen. The catheter system is used for delivery of the embolic composition in a controlled manner for embolizing blood vessels.

2. State Of The Art

In many clinical situations it is desirable to selectively occlude blood vessels for a variety of purposes, such as, the control or prevention of bleeding, the prevention of blood supply to tumors, and the blocking of blood flow within an aneurysm. Embolization of blood vessels has been performed by employing certain polymer compositions and/or particulate including silicone balloons, metallic coils, PA particles, gelatin, sclerosing material, and the like, to selectively block blood flow in the blood vessels.

Intracranial aneurysms are present in between one and nine percent of the population and rupture at a rate of more than 50,000 per year in North America. Intracranial aneurysms are abnormal blood filled dilations of a blood vessel wall which may rupture causing significant bleeding and damage to surrounding brain tissue or death. Traditionally, intracranial aneurysms have been surgically clipped to reduce the risk of rupture by placing a metal clip around the neck of the aneurysm to cut off and prevent further blood flow to the aneurysm. However, many aneurysms cannot be treated surgically because of either the location and configuration of the aneurysm or because the condition of the patient does not permit cranial surgery.

When aneurysms cannot be treated surgically or when surgery is considered to be too risky or invasive, aneurysms may be treated endovascularly with coils. The coils are placed in the aneurysm by extending a catheter endovascularly to the site of the aneurysm and passing single or often multiple platinum or tungsten coils through the catheter into the aneurysm. The coils placed within the aneurysm create a thrombus which occludes the aneurysm and prevents further blood flow to the aneurysm. The treatment of intracranial aneurysms with coils isolates the aneurysm from arterial circulation helping to guard against rupture and further growth of the aneurysm. However, the use of platinum coils to treat intracranial aneurysms may not be a permanent solution because the blood clot around the coils may declot or dissolve due to the dynamic nature of the blood clotting function. Once a clot formed around the coils in an aneurysm declots, the coil can no longer perform its function of occluding the aneurysm. In addition, the coils may become dislodged and enter the patient's blood stream causing blockages at other locations within the vascular system.

Another drawback associated with the use of coils to occlude an aneurysm is that the coils are known to compact over time leaving cavities for subsequent aneurysm growth. In addition, if a subsequent surgical clipping procedure is warranted, it can be difficult to place the clip over the coil mass.

Aneurysms having large necks are not easily treated by either surgical clipping or by coils because the aneurysm neck may have a shape which cannot be completely clipped surgically and the coils may tend to become dislodged from the aneurysm when the neck is particularly large.

One minimally invasive procedure for treating intracranial aneurysms which addresses the problems with the surgical clipping and coil techniques involves the endovascular injection of a liquid embolic composition which solidifies in the aneurysm to occlude the aneurysm. The liquid embolic composition generally includes a water-insoluble, biocompatible polymer and a biocompatible solvent. Once the liquid embolic composition is injected into the aneurysm, the biocompatible solvent dissipates into the blood and the polymer solidifies to occlude the blood flow through the aneurysm.

Typically, liquid embolic compositions include a water insoluble, biocompatible, non-biodegradable polymer dissolved in a biocompatible solvent and preferably these compositions include a radiopaque material which allows the physician to view the embolization procedure by fluoroscopy. Prior to delivery of the embolic composition to the aneurysm, the aneurysm and delivery device are preferably positioned so that the liquid embolic composition will be delivered by gravity into the aneurysm and will remain in the aneurysm (with the aneurysm neck pointing up). As the embolic composition is delivered to the aneurysm, the solvent dissipates from the polymer material causing the polymer material within the aneurysm to solidify.

Depending on the rate at which the liquid embolic material is injected into the blood vessel and the amount of blood flow present, the polymer may remain in liquid form for a period of time while the solvent dissipates into the blood stream. Moreover, the solvent may not be completely dissipated from a center of the polymer mass creating a mass with a solid outer shell and liquid interior. In addition, the solvent concentration at the point of injection may increase to a point where small strings of unsolidified polymer material may separate from the polymer mass and be carried away in the blood stream where it can occlude an undesired vascular location. Since the solvent generally has a density greater than water or blood, gravity may hold the solvent in the aneurysm and prevent the polymer from solidifying.

Accordingly, it would be desirable to provide a method for controlling the solidification of the polymer material during injection. It would also be desirable to provide a method for filling an aneurysm which is not positioned such that gravity may be used to cause the embolic composition to flow into and remain in the aneurysm, since a patient's anatomical position cannot always be in a gravity dependent position.

As disclosed in U.S. patent application Ser. No. 08/730, 701, embolization of a blood vessel with a liquid embolic composition generally includes a preparatory step of flushing a delivery catheter through which the liquid embolic composition is to be delivered with the biocompatible solvent material to remove any aqueous material from the catheter. The removal of any aqueous material from the catheter inhibits solidification of the embolic composition within the catheter during delivery. This preliminary step of flushing with the solvent must be done at a slow flow rate to prevent damage to the blood vessel caused by high concentrations of the solvent which can be toxic and may cause vascular spasms. However, it would be desirable to be able to perform the preliminary flushing of the delivery catheter without concern of causing tissue damage.

SUMMARY OF THE INVENTION

According to one aspect of the invention a catheter system for controlled delivery of polymer compositions includes a multiple lumen catheter having a first lumen and a second lumen for delivery of fluid. A first fluid delivery port delivers fluid to the first lumen and a liquid supply is connected to the first fluid delivery port for delivery of a liquid embolic composition through the first lumen. A second fluid delivery port delivers fluid to the second lumen and a solidification agent supply is connected to the second fluid delivery port for delivery of a solidification agent through the second lumen to enhance solidification of the liquid embolic composition delivered through the first lumen.

According to a further aspect of the invention a catheter for controlled delivery of embolic compositions includes a first tube formed of a DMSO compatible material, a second tube connected to the first tube and an actuator for sliding the first tube longitudinally with respect to the second tube. A first fluid delivery port is connected to a lumen of the first tube for delivery of a liquid embolic composition including a biocompatible, water insoluble, polymer composition dissolved in DMSO. A second fluid delivery port is connected to a lumen of the second tube for delivery of a solidification agent which encourages dissipation of the DMSO and solidification of the polymer composition.

According to an additional aspect of the invention a method of embolizing a vascular site such as an aneurysm with a liquid embolic composition includes the steps of inserting a multiple lumen catheter endovascularly to a vascular site, injecting a liquid embolic composition through a first lumen of the multiple lumen catheter at the vascular site, and controlling solidification of the liquid embolic composition within the vascular site by injecting a solidification agent through a second lumen of the multiple lumen catheter at the vascular site.

In accordance with a further aspect of the present invention, a method for reducing toxic effects of a non-aqueous solvent delivered intravascularly includes positioning a multi-lumen catheter into a vascular site of a mammal, injecting a composition comprising a non-aqueous solvent through a first lumen of the multiple lumen catheter at the vascular site, and injection an aqueous solution through at least a second lumen of the multiple lumen catheter at the vascular site to dilute the non-aqueous solvent and reduce toxic effects of the non-aqueous solvent on surrounding tissue.

In accordance with another aspect of the present invention, a kit for controlled delivery in vivo of a liquid embolic composition includes a liquid embolic composition, and a multiple lumen catheter for delivery of liquid embolic composition through a first lumen and delivery of a solidification agent through a second lumen.

BRIEF DESCRIPTION OF THE DRAWINGS

The invention will be described in greater detail with reference to the accompanying drawings in which like elements bear like reference numbers, and wherein.

DETAILED DESCRIPTION OF THE PREFERRED EMBODIMENTS

Figure 1:
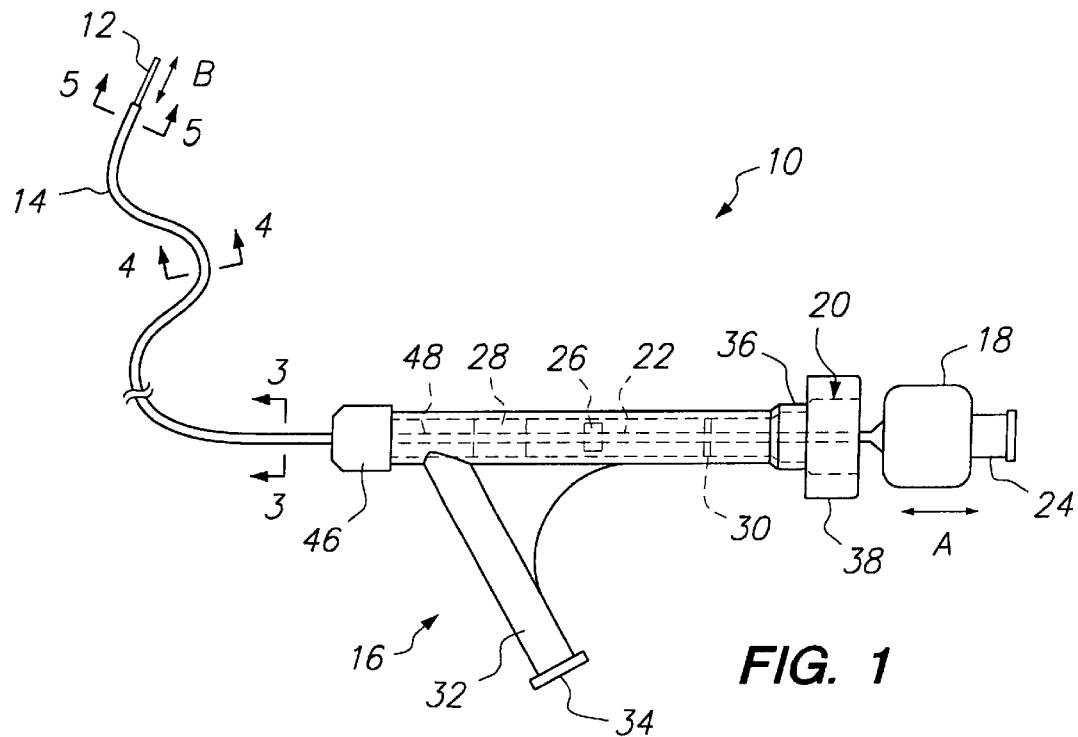
FIG. 1 is a side view of the catheter system according to the present invention.

The catheter system of FIG. 1 includes a catheter having at least two lumens for delivery of a liquid embolic composition through a first lumen and delivery of a solidification agent through a second lumen. The liquid embolic composition and the solidification agent are delivered to the two lumens through a catheter connector which allows adjustment of the relative longitudinal positions of the two lumens. The catheter system is used to embolize vascular sites by controlled solidification of the embolic composition within such sites.

The catheter system 10 includes an inner tube 12, an outer tube 14, and proximal end connector 16 also called a Y-connector or Y-fitting for connection of fluid supplies to the inner and outer tubes. The outer tube 14 is positioned coaxially around the inner tube 12 forming an annular lumen between the inner and outer tubes and an annular outlet of the outer tube. The inner tube 12 is movable within the outer tube 14 by an actuator 18 and can be locked in place with respect to the outer tube by a locking mechanism 20.

The method according to the present invention involves the insertion of the multiple lumen catheter of the catheter system 10 endovascularly to a vascular site such as an aneurysm and injecting a liquid embolic composition through a first lumen while injecting a solidification agent through a second lumen to control solidification of the liquid embolic composition. The controlled solidification of the liquid embolic composition allows the vascular site to be filled more precisely and rapidly, even when the aneurysm is located such that gravity does not cause the liquid embolic to remain in such sites.

Prior to discussing the present invention in further detail, the following terms are defined:

The term "embolic composition" refers to a fluid composition that is injected into a blood vessel and solidifies to fully or partially occlude the vascular site.

The term "embolizing" or "embolization" refers to a process wherein a fluid composition is injected into a blood vessel which, in the case of, for example, aneurysms, fills or plugs the aneurysm sac and/or encourages clot formation so that blood flow into the aneurysm and pressure in the aneurysm ceases, and in the case of arterial venous malformations (AVMs) and arterial venous fistula (AVFs) forms a plug or clot to control/reroute blood flow to permit proper tissue perfusion. Embolization may be used for preventing/controlling bleeding due to lesions (e.g., organ bleeding, gastrointestinal bleeding, vascular bleeding, as well as bleeding associated with an aneurysm). In addition, embolization can be used to ablate diseased tissue (e.g., tumors, etc.) by cutting off its blood supply.

The term "biocompatible polymer" refers to polymers which, in the amounts employed, are non-toxic, chemically inert, and substantially non-immunogenic when used internally in the patient and which are substantially insoluble in blood and other aqueous solutions but are soluble in the fluid composition to the degree necessary to form a solid mass in vivo.

The term "contrast agent" refers to both water insoluble and aqueous based contrast agents which are visible by x-ray, fluoroscopy, CT scan, MRI, or the like.

The term "biocompatible solvent" refers to solvents capable of dissolving the selected biocompatible polymer which are miscible or soluble in aqueous compositions (e.g., blood). Suitable biocompatible solvents include ethanol, dimethylsulfoxide (DMSO), ethyl lactate, acetone, and the like as well as aqueous mixtures thereof having no more than about 30 percent water. When employed at this level, the amount of water is sufficiently small that the dissolved polymer precipitates upon contact with the blood. Preferably, the biocompatible solvent is anhydrous and, even more preferably, the biocompatible solvent is anhydrous dimethylsulfoxide (DMSO).

The term "solidification agent" refers to a liquid composition which when in proximity to the liquid embolic composition, increases the rate at which the liquid embolic composition solidifies. Examples of such solidification agents include sterile water, sterile saline, Dextrose 5% water (D5W), lactated Ringers solution, contrast agents and the like.

The term "catheter" includes both catheters and microcatheters. The catheters and microcatheters are designed for use in the highly tortuous blood vessels of the body, such as, intracranial blood vessels. By highly tortuous, we mean the typical tortuosity encountered in the vascular pathway from a remote access site such as the femoral artery to target sites deep within in the coronary, renal, and cerebral vasculature. Specific embodiments may be constructed for access into target sites involving pathologically tortuous blood vessels, and by pathological tortuosity, we mean that the vascular pathway from a remote access site such as the femoral artery to target sites involves turns in excess of 90° when branching off from one blood vessel to another blood vessel (paths which branch off the proceeding vessel at angles greater than a right angle), and where the total path length within the target tissue is at least about 5 cm and is also characterized as being accessible by a guidewire 0.018 inches or smaller, but being too delicate and/or tortuous for accessing by a significantly larger diameter guidewire.

Figure 2:
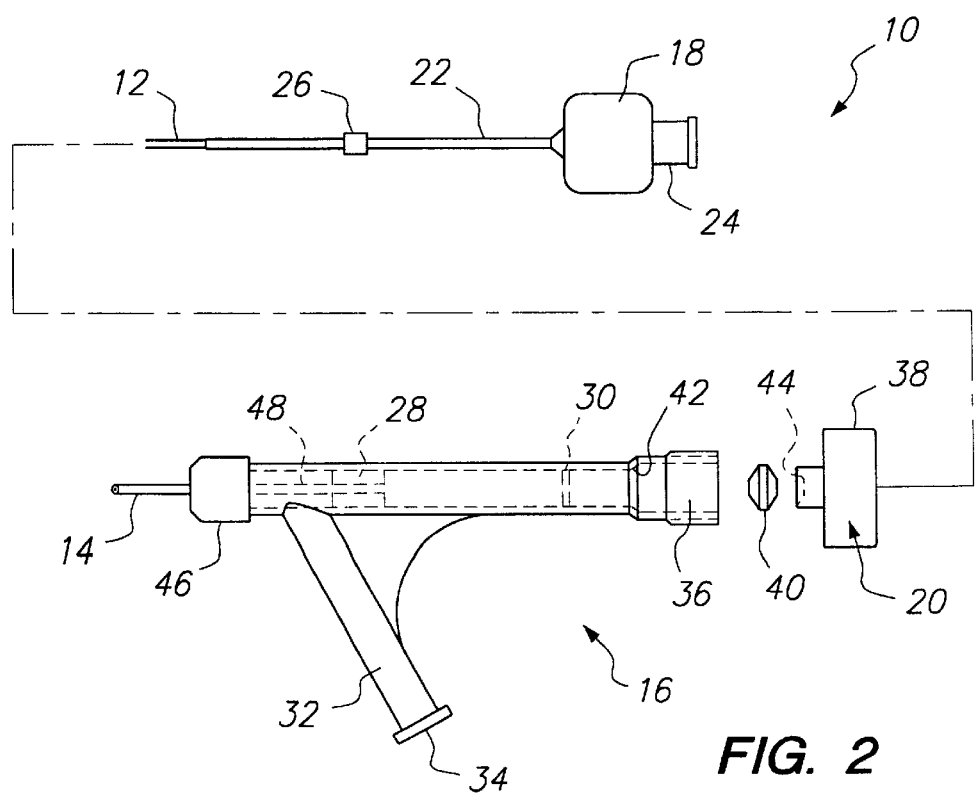
FIG. 2 is an exploded side view of the catheter system of FIG. 1.

FIGS. 1 and 2 illustrate the catheter system 10 according to the present invention through which the liquid embolic composition and the solidification agent are injected into a vascular site to achieve controlled solidification of the liquid embolic composition within the blood vessel. As illustrated in the exploded view of FIG. 2, a proximal end of the inner tube 12 extends through a rigid tube 22 which stabilizes the proximal end of the inner tube. The proximal ends of the rigid tube 22 and the inner tube 12 are connected to the actuator 18. The actuator 18 is positioned on a first luer hub 24 and includes a substantially flat rectangular manipulator which is grasped by the physician to move the inner tube 12 longitudinally within the outer tube 14. The rigid tube 22 is positioned within the connector 16 with a stop 26 of the rigid tube arranged between corresponding first and second stops 28, 30 within the connector 16. The first and second stops 28, 30 of the connector 16 engage the stop 26 of the rigid tube 22 to limit the longitudinal motion of the inner tube 12 with respect to the outer tube 14.

According to an alternative embodiment, proximal motion of the actuator 18 and the inner tube 12 is limited by engagement of the stop 26 with the second stop 30. Distal motion of the inner tube 12 with respect to the outer tube 14 is limited by engagement of the actuator 18 with the locking mechanism 20.

The first luer hub 24 is positioned proximally of the actuator 18 and provides mating means for mating with a syringe (not shown) filled with the liquid embolic composition. A preferred luer hub/syringe combination is illustrated in U.S. patent application Ser. No. 08/866,208 which is incorporated herein by reference in its entirety. Although the liquid embolic composition would generally be delivered to the catheter by a syringe in a quantity which may be continuously controlled by the physician, it may also be injected by other means such as a high pressure injector or pump.

The catheter connector 16 includes a Y-arm 32 with a second luer hub 34 which provides mating means for mating with a supply of the solidification agent. The Y-arm 32 extends from a side of the main body of the connector 16 for delivery of the solidification agent to the interior of the connector. From the interior of the connector 16 the solidification agent passes into the annular lumen between the outer tube 14 and the inner tube 12. The outer tube 14 is connected to the connector 16 by a distal end cap 46 of the connector. The outer tube 14 may be connected by a compression fit by trapping the proximal end of the tube between the connector 16 and the end cap 46 by a threaded connection. The outer tube 14 may also be connected to the connector by adhesive bonding, insert molding, and the like. The solidification agent may be delivered to the outer tube 14 through the Y-arm 32 from a variety of sources, such as, a gravity feed saline bag, a pump, a high pressure injector, or a syringe.

An anti-kinking feature of the present invention is provided to prevent kinking of the inner tube 12 as it is pushed distally within the outer tube 14. The anti-kinking feature includes an outer rigid tube 48 which is press fit within the stop 28. The stop 28 is in turn press fit within the main body of the connector 16. The inner rigid tube 22 slides within the somewhat larger outer rigid tube 48 to guide the inner tube 12 within the outer tube 14 without kinking. When the inner rigid tube 22 has been moved proximally until the stop 26 of the rigid tube engages the stop 30, an end of the inner rigid tube remains inside the outer rigid tube 48. Without the rigid tubes 22, 48, it would not be possible to slide the inner tube 12 into the outer tube 14 because the flexible inner tube would fold up within the connector 16.

The outer rigid tube 48 extends from the stop 28 toward the distal end cap 46. However, the outer rigid tube 48 ends before a proximal end of the outer tube 14 providing a gap. Accordingly, the fluid injected through the luer hub 34 passes around the outer rigid tube 48, through the gap between outer rigid tube and the outer tube 14, and into the outer tube.

The locking mechanism 20 for locking the relative longitudinal positions of the inner tube 12 and the outer tube 14 is best shown in the exploded view of FIG. 2. The locking mechanism 20 includes an externally threaded end 36 of the connector 16, a rotatable cap 38 having internal threads, and a resilient sealing member 40. When the connector 16 is assembled with the inner tube 12 positioned within the outer tube 14 the sealing member 40 is positioned around the rigid tube 22 connected to the inner catheter tube 12. The sealing member 40 has a shape which includes an annular tapered surface at each end and a through bore for receiving the rigid tube 22. The opposite annular tapered surfaces of the sealing member 40 engage correspondingly tapered surfaces 42, 44 inside the connector 16 and inside a distal end of the rotatable cap 38, respectively. In a preferred embodiment of the present invention, the sealing member 40 is a type of seal called a Tuohy-Borst seal.

The rigid tube 22 is placed inside the connector 16 such that the inner tube 12 is slidable within the outer tube 14, and the rigid tube 22 is slidable within the connector and the rigid tube 48. As the rotatable cap 38 is tightened onto the threaded end 36 of the connector 16 the sealing member 40 is compressed between the tapered internal surface 42 of the connector 16 and the tapered internal surface 44 of the cap. As the sealing member 40 is compressed longitudinally it expands radially inwardly and radially outwardly to lock the rigid tube 22 in place within the connector 16 and to provide a fluid tight seal between the interior surfaces of the connector and the exterior surface of the rigid tube. In this manner, the locking mechanism 20 freezes the ends of the inner and outer tubes 12, 14 with respect to each other.

The inner and outer tubes 12, 14 for use in the present invention are particularly designed to have sufficient rigidity to be inserted with or without a guide wire to a location within a blood vessel for embolization and to have sufficient flexibility at the distal end to prevent damage to tissue. In order to achieve these objectives, of rigidity at the proximal end and flexibility at the distal end, the inner and outer tubes 12, 14 may each be formed of two segments of differing flexibilities joined together. The joints between the distal and proximal segments of the inner and outer tubes are longitudinally staggered resulting in the three different cross sections of the catheter illustrated in FIGS. 3–5. Although the invention is described as employing catheter segments joined by joints, the catheter segments of differing cross-sections and flexibilities may be extruded together as a single piece to avoid the need for joints. Alternatively, the inner and outer tubes 12, 14 may have a continuously changing flexibility along their lengths.

Figure 3:
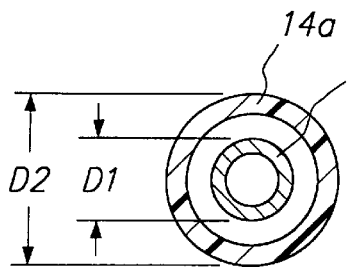
FIG. 3 is an enlarged cross-sectional view of the multiple lumen catheter taken along line 3—3 of FIG. 1.

As shown in FIG. 3, a proximal segment 12a of the inner tube 12 is formed of a material having a preferred durometer of approximately 40 Shore D to 90 Shore D, more preferably approximately 60 Shore D to 80 Shore D, and a diameter D1. A proximal segment 14a of the outer tube 14 is formed of a material having a preferred durometer of approximately 40 Shore D to 90 Shore D, more preferably approximately 60 Shore D to 80 Shore D, and a diameter D2.

Figure 4:
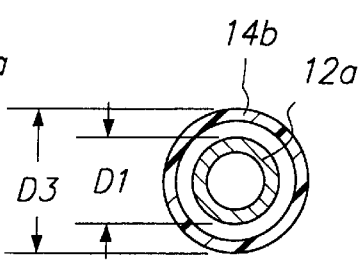
FIG. 4 is an enlarged cross-sectional view of the multiple lumen catheter taken along line 4—4 of FIG. 1.

The proximal segment 14a of the outer tube 14 having the diameter D2 is fused to a distal segment 14b of the outer tube which has a smaller diameter D3, shown in FIG. 4. The distal segment 14b of the outer tube 14 has a durometer which is smaller than that of the proximal segment 14a. Preferably, the durometer of the distal segment 14b is approximately 40 Shore A to 45 Shore D more preferably approximately 80 Shore A to 100 Shore A. The transition between the segments 14a, 14b of the outer tube 14 occurs between the section line 3—3 and the section line 4—4 in FIG. 1. This transition between the distal and proximal segments 14a, 14b of the outer tube 14 is located along the length of the catheter as required to allow the catheter to be tracked along a tortuous path, preferably the transition is between 15 and 20 cm from the distal end of the catheter.

Figure 5:
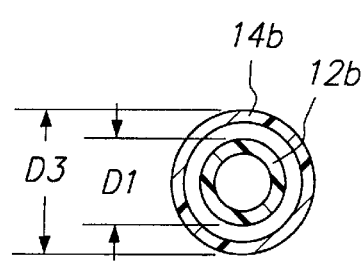
FIG. 5 is an enlarged cross-sectional view of the multiple lumen catheter taken along line 5—5 of FIG. 1.

The proximal segment 12a of the inner tube 12 is fused to a distal segment 12b of the inner tube, shown in FIG. 5. The proximal and distal segments 12a, 12b of the inner tube preferably have the same diameter D1 but are formed of different materials with different flexibilities. The distal segment 12b of the inner tube 12 preferably has a durometer of approximately 40 Shore A to 45 Shore D, more preferably approximately 80 Shore A to 100 Shore A.

One example of a multiple lumen catheter employed in the present invention has a usable length of about 150 cm, a proximal portion of the outer tube which is about 3.6 French and a distal portion of the outer tube which is about 2.6 French. The wall thicknesses of the inner and outer tubes vary from about 0.003 inches (0.008 cm) to about 0.005 inches (0.013 cm), with the proximal portion of the outer tube having the largest wall thickness. The proximal portions of the inner and outer tubes are formed of high density polyethylene having a durometer of about 70 Shore D. The more flexible distal portions of the inner and outer tubes are formed of about 40% low density polyethylene and about 60% Engage by Dow (polyolefin) having a durometer of about 35 Shore D. This catheter configuration has been described only as an example.

Catheters having a size of between about 1.5 and 5.0 French may be used for treatment of aneurysms and other sizes may also be used for other types of treatments of vascular sites. The catheters may also be braided or coil reinforced and formed of a wide variety of materials. Braided or otherwise reinforced catheters provide kink resistance, crush resistance, and steerability.

The inner tube 12 is movable from an extended position in which the inner tube extends from the distal end of the outer tube 14 by up to about 30 mm to a retracted position in which the inner tube distal end is even with or inside the distal end of the outer tube 14. Movement of the actuator 18 in the direction of arrow A in FIG. 1 provides a corresponding movement of the distal end of the inner tube 12 in the direction of the arrow B. The inner and outer tubes 12, 14 preferably experience minimal elongation or compression such that the distance of travel of the actuator 18 is substantially the same as the distance of travel of the distal end of the inner tube 12.

The tip of the catheter is preferably shaped prior to use by the physician to a desired shape for the particular location and configuration of the vasculature to be treated. The tip of the catheter is shaped by placing a tip shaping mandrel in the lumen of the inner tube 12. A sleeve may also be placed in the lumen between the outer tube 14 and the inner tube 12 during shaping to support the outer tube. The catheter tip with the mandrel and the sleeve is then shaped to a desired curvature by the physician and subsequently steam heated to hold the curvature once the mandrel and sleeve have been withdrawn.

The method according to the present invention involves the injection of a solidification agent to control the solidification of the embolic composition within a blood vessel. The solidification agent allows for rapid, controlled solidification of the embolic composition and places more control of the embolization procedure in the hands of the physician.

One example of a liquid embolic composition for embolizing aneurysms includes a biocompatible, water insoluble polymer, a contrast agent, and a biocompatible solvent such as dimethylsulfoxide (DMSO). Examples of such embolizing compositions are described in U.S. Pat. No. 5,667,767, which issued Sep. 16, 1997, U.S. Pat. No. 5,580,568, which issued on Dec. 3, 1996, and allowed U.S. patent application Ser. No. 08/688,050 now U.S. Pat. No. 5,695,480 each of which are incorporated herein by reference in their entirety.

Figure 6:
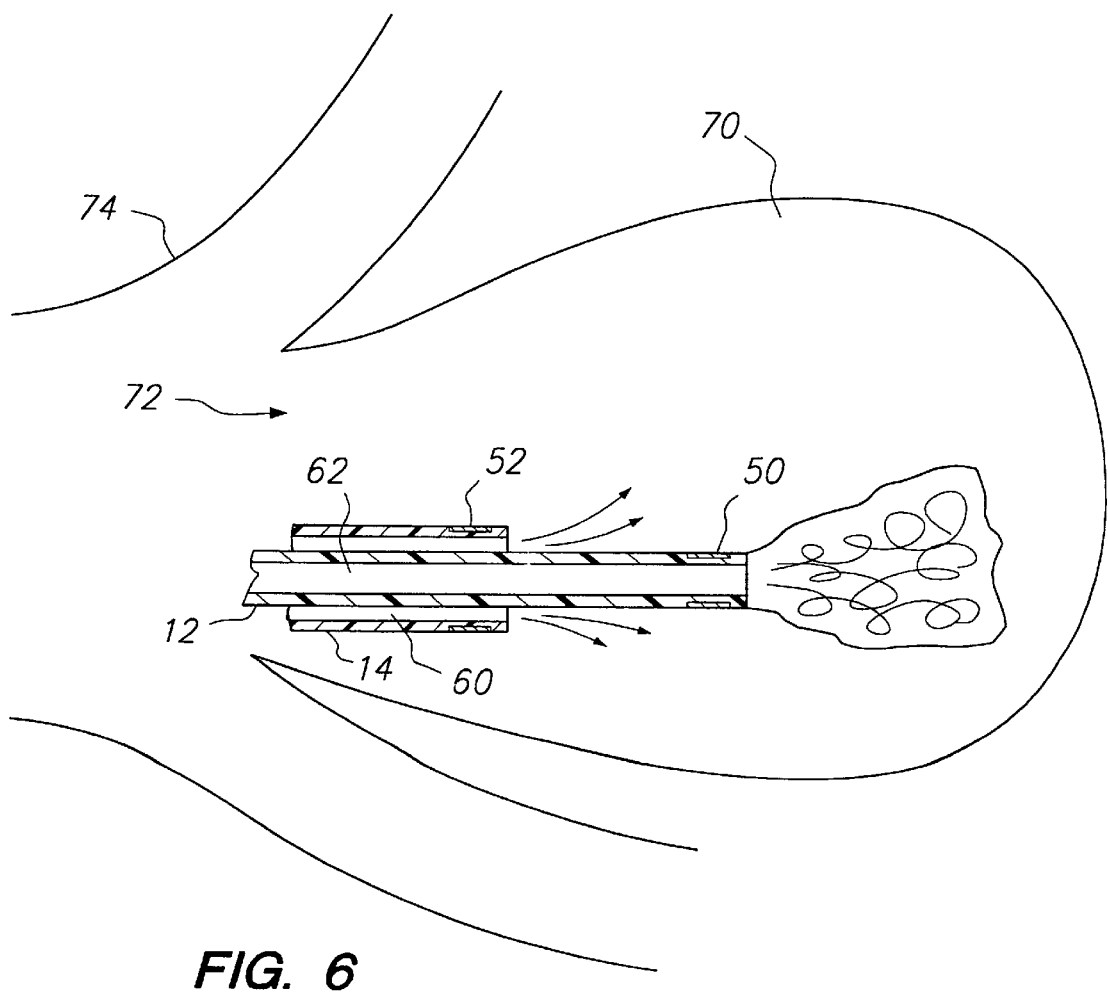
FIG. 6 is an enlarged side cross-sectional view of an aneurysm being treated by the method according to the present invention.

FIG. 6 illustrates the use of the method and apparatus according to the present invention to occlude an aneurysm 70 having a relatively large neck 72 which has formed at a branch in a blood vessel 74. The aneurysm 70 is treated by inserting the multiple lumen catheter of FIG. 1 endovascularly until a distal end of the catheter is positioned within or near the aneurysm or the neck 72 of the aneurysm. The position of the catheter tip will vary depending on the aneurysm shape, size, and flow pattern. A guide wire (not shown) positioned in the inner tube 12 may or may not be used to guide the catheter through the blood vessels. Other methods of tracking the catheter to the aneurysm include steerable systems in which the catheter tip is steered, flow directed systems, or sheath directed systems in which the catheter is delivered through a sheath. The insertion of the catheter is generally performed under fluoroscopic visualization in a known manner.

As shown in FIG. 6, the distal ends of the inner and outer tubes 12, 14 each have a radiopaque marker 50, 52, respectively, to allow the physician to view the relative positions of the distal ends of the two catheter tubes and the position of the catheter tubes with respect to the aneurysm 70. The radiopaque markers 50, 52 may be formed either at the inner or outer diameters of the tubes 12, 14. While tracking the catheter through a typical tortuous path, the inner tube 12 may be extended from the end of the outer tube 14 to improve the flexibility and tracking of the catheter distal end.

Prior to delivery of the liquid embolic composition to the aneurysm 70, the lumen 62 of the inner tube 12 is preferably flushed with a barrier fluid to remove any aqueous material, such as blood, saline, or contrast agent from the inner tube which may cause the embolic composition to solidify within the catheter and block the catheter. The catheter does not need to be entirely primed with the barrier fluid as long as the column of barrier fluid is of a sufficient length to prevent contact between the liquid embolic composition and any aqueous material in the catheter. The barrier fluid may be the biocompatible solvent or another fluid providing a barrier between aqueous fluids and the liquid embolic composition.

High concentrations of organic solvents such as DMSO, ethanol and others when used as barrier fluids can be toxic to tissue and may cause vascular spasms. In order to avoid the high solvent concentrations which are toxic to tissue, a dilution liquid is injected through the annular lumen 60 between the inner and outer tubes 12, 14 during injection of the barrier fluid. The dilution liquid may be the same liquid as the solidification agent, e.g., saline, or may a different liquid.

The injection of a dilution agent minimizes the effect of the toxicity of an organic solvent and greatly increases the solvent injection flow rate which can be used safely. Preferably, the dilution agent is injected through the lumen 60 of the outer tube 14 before or as soon as the solvent begins to exit the inner lumen 62 before any of the embolic composition has been injected. The dilution agent causes the solvent to diffuse in the vessel treatment area at a much higher rate, and therefore, the concentration of the solvent in contact with the tissue is greatly decreased. A contrast agent may be used as the dilution agent to help visualize flow characteristics of the aneurysm and determine optimum catheter placement within the aneurysm.

According to the method of the present invention illustrated in FIG. 6, the aneurysm 70 is treated by injection of the liquid embolic composition into the aneurysm 70 through the lumen 62 of the inner tube 12 by a syringe or other delivery mechanism attached to the luer connection 24. The solidification agent, e.g., saline, is injected through the lumen 60 of the outer tube 14 in tandem or just subsequent to the injection of the liquid embolic composition. The solidification agent may be injected in a continuous or a pulsatile manner. The solidification agent washes the area of the aneurysm of blood which has become saturated with solvent, replacing it with fresh solidification agent. The washing action of the solidification agent is used to remove blood and other viscous fluids in the aneurysm which are otherwise difficult to displace. In addition, the solidification agent provides a diffusion bed of solidification agent and increases the diffusion gradient which improves the diffusion of the solvent from the embolic composition as the composition solidifies in a coherent mass.

Without the use of the solidification agent the solvent concentration gradient between the liquid embolic composition being injected and the surrounding blood decreases as the solvent dissipates from the embolic composition slowing the rate at which the solvent diffuses from the embolic composition. The solidification agent is used to increase the solvent concentration gradient which causes the solvent diffusion rate to increase.

According to an alternative embodiment of the invention, the liquid embolic composition and solidification agent are injected alternately rather than simultaneously. The injection of liquid embolic composition alone will form a nearly spherical shape. The liquid embolic injection may then be discontinued while the solidification agent is injected to solidify the spherically shaped mass of liquid embolic. The timing of the injection of the liquid embolic composition and the solidification agent may be varied to achieve different results.

The inner tube 12 is slidable within the outer tube 14 so that the tip of the inner tube can be extended to different lengths from the distal end of the outer tube to further control the solidification of the embolic composition depending on the aneurysm size, shape, and flow characteristics. The injection of a fluid through the annulus between the inner and outer tubes 12, 14 may also be used to aid in the movement of the inner tube inside the outer tube by creating a moving fluid column which reduces friction between the tubes. The use of fluid as a friction reducing mechanism may be particularly useful when the catheter has been tracked through a typically tortuous path such as that provided by the blood vessels of the brain.

Figure 7:
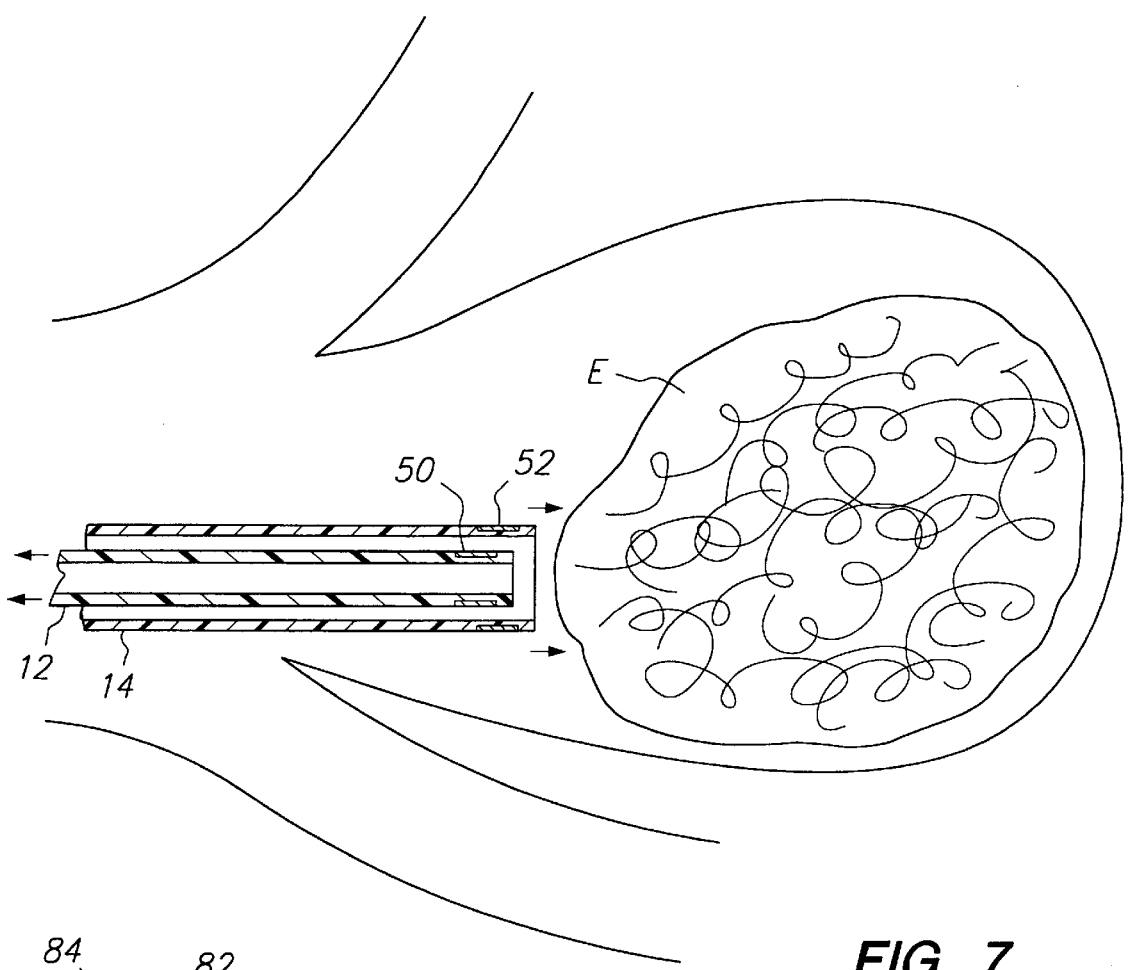
FIG. 7 is an enlarged side cross-sectional view of an aneurysm showing the detachment of an embolic mass from the catheter.

When embolization of the aneurysm is completed or is halted for some other reason, the outer tube 14 serves as a lip to disconnect the embolic mass from the catheter by retracting the inner tube 12 into the outer tube. The separation of a coherent solid mass of embolic composition E from the end of the catheter is illustrated in FIG. 7. Without the detachment mechanism provided by the movable inner tube 12, it may be difficult for the physician to separate the embolic mass E from the catheter without causing trauma to the surrounding tissue. The detachment may be provided by any one or more of the following steps: 1) retracting the inner tube 12 into the outer tube 14; 2) advancing the outer tube over the inner tube; or 3) injecting solidification agent to detach the embolic mass from the outer tube.

In order to visualize the flow in the area being treated, including the flow into and out of the aneurysm, the dilution agent and/or the solidification agent can be combined with a contrast agent and injected alone prior to injection of the liquid embolic composition. Further, washout can be visualized by injection of contrast agent through the inner lumen while solidification agent is injected through the annular lumen between the inner and outer tubes 12, 14.

Although the present invention has been described as employing a coaxial catheter having coaxial lumens, the present invention may also employ other types of multiple lumen catheters such as those shown in FIGS. 8–11. Additional multiple lumen catheter configurations other than those shown may also be used, including catheters having multiple lumens for delivery of the liquid embolic composition and catheters having multiple lumens for delivery of the solidification agent. Further, two independent catheters may be used for separate delivery of the liquid embolic composition and the solidification agent to achieve the controlled solidification of the embolic composition according to the method of the present invention.

Figure 8:
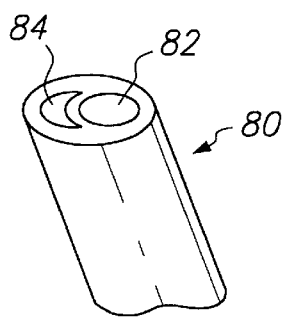
FIG. 8 is an enlarged perspective view of a distal end of a catheter according to a first alternative embodiment of the invention.

A multiple lumen catheter 80 illustrated in FIG. 8 has a first lumen 82 and a second lumen 84 positioned side by side. In this side by side embodiment, the liquid embolic composition is injected through the first lumen 82 while the solidification agent is injected through the second lumen 84.

Figure 9:
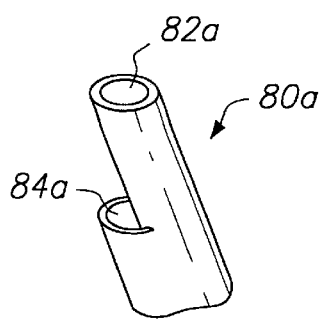
FIG. 9 is an enlarged perspective view of a distal end of a catheter according to a second alternative embodiment of the invention.

As shown in FIG. 9, the outlets of the two lumens 82a, 84a may be longitudinally staggered so that the solidification agent injected through the second lumen 84a washes around the outlet of the first lumen 82a delivering the embolic composition. In addition, the side-by-side embodiments of FIGS. 8 and 9 may include means for adjusting the longitudinal position of one of the lumens with respect to the other lumen.

Figure 10:
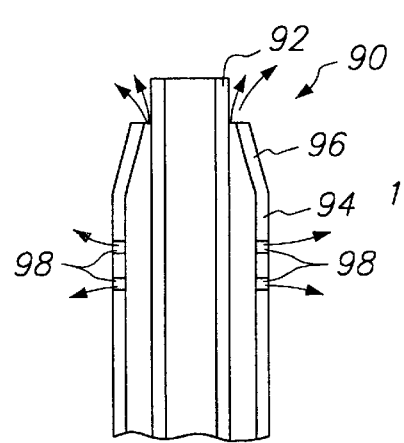
FIG. 10 is an enlarged cross-sectional view of the distal end of a catheter according to a third alternative embodiment of the invention.

FIG. 10 illustrates another alternative embodiment of a multiple lumen catheter 90 having an inner tube 92 and an outer tube 94 coaxially surrounding the inner tube. The outer tube 94 includes a distal tapered portion 96 and a plurality of openings 98 or side holes. The liquid embolic composition is delivered through the inner tube 92 while the solidification agent is delivered through the outer tube 94 and exits both and through end of the outer tube and through the openings 98. The tapered portion 96 of the outer tube 94 causes the solidification agent to be injected at an increased velocity along the inner tube 92 and washes the liquid embolic as it is injected from the inner tube. The size and number of the openings 98 and the degree of taper may be varied to provide different amounts of flow through the end of the outer tube 94 and through the openings.

Figure 11:
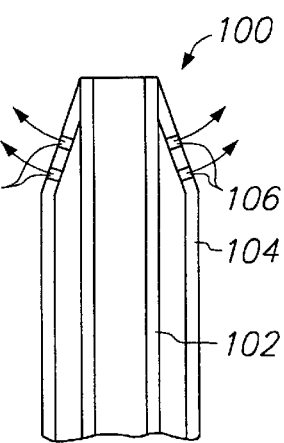
FIG. 11 is an enlarged cross-sectional view of a distal end of a catheter according to a fourth alternative embodiment of the invention.

FIG. 11 illustrates a further alternative embodiment of a multiple lumen catheter 100 in which an outer coaxial tube 104 is fused to an inner coaxial tube 102 at a distal end of the catheter. One or more openings 106 or side holes are provided in a side wall of the outer tube 104 for delivery of the solidification agent. The openings 106 may be particularly designed to deliver the solidification agent in a desired delivery pattern by variation of the number, size, and location of the openings.

Although the present invention has been described in detail for use in treatment of aneurysms, it can also be used in a variety of other applications where controlled solidification of a liquid embolic composition is desired. For example, the present invention may be used to occlude a blood vessel in order to block the blood flow to a tumor to ablate tumorous tissue. The present invention may be used to control bleeding in blood vessels by occluding a blood vessel. Further, the present invention may be used to control the solidification of a biocompatible polymer which is used for reversible sterilization or for bulking of tissues to treat urinary incontinence.

The injection of the solidification agent to control the solidification of the embolic composition according to the present invention is particularly useful in situations where high flow rates may carry the liquid embolic away from the embolization site before it is solidified in a mass, for example an AVF, and for situations where the position of the formation to be filled with the embolic composition does not allow the liquid embolic composition to remain by gravity in the formation. The invention may also be particularly useful in situations where the fluid flow is very low and the solvent is not carried away as it dissipates from the embolic composition.

The catheter for use in the present invention particularly the inner tube 12, and also the connector 16 and the actuator 18, are formed of solvent compatible materials. According to a preferred embodiment of the invention in which the solvent is DMSO, the catheter elements which may come into contact with the solvent are DMSO compatible. Examples of DMSO compatible materials and some of the preferred durometers of these materials for use in a catheter include polyolefins, such as, polyethylene (80A–80D), polyester polyether block copolymer (30D–80D), Alcryn (chlorinated polyolefin) (60A–80A), Pebax (polyamide polyether block copolymer) (25D–70D); fluoropolymers, such as, PTFE (such as Teflon), ETFE, and SEBS (styrene ethylene butadiene styrene); silicones; interpenetrating networks of silicone; and nylons (6/6, 6/10, and 6/12); and polyimide.

The inner and outer tubes 12, 14 are preferably coated with lubricous coatings both on their inner and outer diameters. In particular, a lubricous coating on the outer diameter of the outer tube 14 assists the insertion of the catheter, while lubricous coatings on the inner diameter of the outer tube and on the outer diameter of the inner tube 12 improve the longitudinal motion of the inner tube within the outer tube. A lubricous coating on the inner diameter of the inner tube 12 will improve guidewire movement within the catheter. The lubricous coating on the inner diameter of the inner tube 12 should be compatible with the biocompatible solvent.

The inner and outer rigid tubes 22, 48 within the connector 16 of the present invention may also include a keyed slot extending substantially along their lengths to prevent the relative rotation of the inner and outer tubes 12, 14 at their proximal end. For example, the inner rigid tube 22 may include an external longitudinal groove which receives an internal longitudinal rib of the outer rigid tube 48.

Suitable biocompatible polymers for use in the liquid embolic composition of the present invention include, by way of example, non-biodegradable polymers such as cellulose acetates (including cellulose diacetate), ethylene vinyl alcohol copolymers, hydrogels (e.g., acrylics), polyacrylonitrile, polyvinylacetate, cellulose acetate butyrate, nitrocellulose, copolymers of urethane/carbonate, copolymers of styrene/maleic acid, and mixtures thereof. Other suitable biocompatible polymers include, for example, biodegradable polymers such as linear-chain polymers such as polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyhydroxybutyrates, polyhydroxyvalerates, polyalkylene oxalates, polyalkylene succinates, poly(malic acid), poly(amino acids), polyhydroxycellulose, chitin, chitosan, and copolymers, terpolymers and combinations thereof.

Preferably, the biocompatible polymer does not cause adverse inflammatory reactions when employed in vivo.

The particular biocompatible polymer employed is selected relative to the viscosity of the resulting polymer solution, the solubility of the biocompatible polymer in the biocompatible solvent, and the like. Such factors are well within the skill of the art.

Preferred biocompatible polymers include cellulose diacetate and ethylene vinyl alcohol copolymer. Cellulose diacetate polymers are either commercially available or can be prepared by art recognized procedures. In a preferred embodiment, the number average molecular weight, as determined by gel permeation chromatography, of the cellulose diacetate composition is from about 25,000 to about 100,000 more preferably from about 50,000 to about 75,000 and still more preferably from about 58,000 to 64,000. The weight average molecular weight of the cellulose diacetate composition, as determined by gel permeation chromatography, is preferably from about 50,000 to 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by mere adjustment of the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the embolizing properties of the composition. Such additional monomers include, by way of example only, maleic anhydride, styrene, propylene, acrylic acid, vinyl acetate and the like.

Ethylene vinyl alcohol copolymers are either commercially available or can be prepared by art recognized procedures. Preferably, the ethylene vinyl alcohol copolymer composition is selected such that a solution of 6 weight percent of the ethylene vinyl alcohol copolymer, 25 weight percent of a tantalum contrast agent in DMSO has a viscosity equal to or less than 60 centipoise at 20° C. As is apparent to one skilled in the art, with all other factors being equal, copolymers having a lower molecular weight will impart a lower viscosity to the composition as compared to higher molecular weight copolymers. Accordingly, adjustment of the viscosity of the composition as necessary for catheter delivery can be readily achieved by mere adjustment of the molecular weight of the copolymer composition.

As is also apparent, the ratio of ethylene to vinyl alcohol in the copolymer affects the overall hydrophobicity/hydrophilicity of the composition which, in turn, affects the relative water solubility/insolubility of the composition as well as the rate of precipitation of the copolymer in an aqueous solution (e.g., blood). In a particularly preferred embodiment, the copolymers employed herein comprise a mole percent of ethylene of from about 25 to about 60 and a mole percent of vinyl alcohol of from about 40 to about 75. These compositions provide for requisite precipitation rates suitable for use in embolizing blood vessels.

While the invention has been described in detail with reference to a preferred embodiment thereof, it will be apparent to one skilled in the art that various changes and modifications can be made, and equivalents employed, without departing from the spirit and scope of the invention.

What is claimed is:

1. A catheter for controlling solidification in vivo of liquid embolic compositions comprising:

(a) a first tube formed of a DMSO compatible material, the first tube having a lumen;

(b) a second tube connected to the first tube, the second tube having a lumen, wherein the second tube coaxially surrounds the first tube;

(c) an actuator for sliding the first tube longitudinally with respect to the second tube;

(d) a first fluid delivery port connected to the lumen of the first tube for delivery of a liquid embolic composition which composition comprises a biocompatible, water-insoluble polymer dissolved in DMSO, the first delivery port formed of a DMSO compatible material;

(e) a second fluid delivery port connected to the lumen of the second tube for delivery of a solidification agent which encourages solidification of the liquid embolic composition; and an anti-kinking mechanism for preventing kinking of the first tube as it slides in the second tube, the anti-kinking mechanism including a rigid tube connected to the first tube and a sleeve, wherein the rigid tube is slidable within the sleeve.

2. The catheter according to claim 1, further comprising a locking mechanism for locking a longitudinal position of the first tube with respect to the second tube.

3. The catheter according to claim 1, wherein the first and second tubes each have a proximal portion with a durometer of between about 40 Shore D and 90 Shore D.

4. The catheter according to claim 3, wherein the first and second tubes each have a distal portion with a durometer of between about 40 Shore A and 45 Shore D.

5. The catheter according to claim 4, wherein a joint between the distal and proximal portions of the first tube is longitudinally displaced from a joint between the distal and proximal portions of the second tube at all relative positions of the catheter which are achieved by manipulation of the actuator.

6. The catheter according to claim 1, wherein a distal end of the second tube includes a plurality of side holes for delivery of the solidification agent.

7. A catheter for controlling solidification in vivo of liquid embolic compositions comprising:

(a) a first tube formed of a DMSO compatible material, the first tube having a lumen;

(b) a second tube connected to the first tube, the second tube having a lumen;

(c) an actuator for sliding the first tube longitudinally with respect to the second tube;

(d) a first fluid delivery port connected to the lumen of the first tube for delivery of a liquid embolic composition which composition comprises a biocompatible, water-insoluble polymer dissolved in DMSO, the first delivery port formed of a DMSO compatible material;

(e) a second fluid delivery port connected to the lumen of the second tube for delivery of a solidification agent which encourages solidification of the liquid embolic composition; and wherein a joint is provided between the distal and proximal portions of the first tube and the joint is longitudinally displaced from a joint which is provided between the distal and proximal portions of the second tube at all relative positions of the catheter which are achieved by manipulation of the actuator.

8. The catheter according to claim 7, wherein the second tube coaxially surrounds the first tube.

9. The catheter according to claim 8, wherein the second tube has a distal end including a plurality of side holes for delivery of the solidification agent.

10. The catheter according to claim 8, further comprising an anti-kinking mechanism for preventing kinking of the first tube as it slides in the second tube, the anti-kinking mechanism including a rigid tube connected to the first tube and slidable within a sleeve.

11. The catheter according to claim 7, further comprising a locking mechanism for locking a locking a longitudinal position of the first tube with respect to the second tube.

* * * * *